(12) United States Patent
Stridfeldt et al.

(10) Patent No.: US 9,925,096 B2
(45) Date of Patent: Mar. 27, 2018

(54) ABSORBENT PRODUCT COMPRISING AN ODOR CONTROL MATERIAL

(71) Applicant: SCA Hygiene Products AB, Göteborg (SE)

(72) Inventors: Chatrine Stridfeldt, Göteborg (SE); Ingrid Gustafson, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 15/104,170

(22) PCT Filed: Dec. 20, 2013

(86) PCT No.: PCT/SE2013/051602
§ 371 (c)(1),
(2) Date: Jun. 13, 2016

(87) PCT Pub. No.: WO2015/094067
PCT Pub. Date: Jun. 25, 2015

(65) Prior Publication Data
US 2017/0027779 A1    Feb. 2, 2017

(51) Int. Cl.
*A61F 13/84* (2006.01)
*A61L 15/46* (2006.01)
(Continued)

(52) U.S. Cl.
CPC .......... *A61F 13/8405* (2013.01); *A61F 13/84* (2013.01); *A61L 15/18* (2013.01);
(Continued)

(58) Field of Classification Search
CPC ............ A61F 13/51113; A61F 13/8405; A61F 2013/51076; A61F 2013/5109;
(Continued)

(56) References Cited

U.S. PATENT DOCUMENTS 3,340,875 A    9/1967 Dudley
4,992,326 A    2/1991 Dabi
(Continued)

FOREIGN PATENT DOCUMENTS

CN    101304770 A    11/2008
CN    101325981 A    12/2008
(Continued)

OTHER PUBLICATIONS

The extended European Search Report dated Jun. 13, 2016, by the European Patent Office in related European Patent Application No. 12887897.2-1308. (6 pages).
(Continued)

*Primary Examiner* — Lynne Anderson
(74) *Attorney, Agent, or Firm* — Buchanan Ingersoll & Rooney PC

(57) ABSTRACT

Absorbent product having a liquid permeable surface and a liquid impermeable opposite surface, the absorbent product including an odor control material, the odor control material including a carrier material and a plurality of odor control particles adhered to the carrier material. The carrier material has a first surface located towards the liquid permeable surface of the absorbent product and a second opposite surface located towards the liquid impermeable surface of the absorbent product. The plurality of odor control particles are bonded to the second surface of the carrier material with a water soluble binder substance wherein the binder substance at least partly dissolves when in contact with an aqueous solution.

14 Claims, 3 Drawing Sheets

(51) Int. Cl.
*A61L 15/18* (2006.01)
*A61L 15/24* (2006.01)
*A61L 15/26* (2006.01)
*A61L 15/28* (2006.01)
*A61L 15/42* (2006.01)
*A61F 13/51* (2006.01)

(52) U.S. Cl.
CPC .............. *A61L 15/24* (2013.01); *A61L 15/26* (2013.01); *A61L 15/28* (2013.01); *A61L 15/425* (2013.01); *A61L 15/46* (2013.01); *A61F 2013/5109* (2013.01); *A61F 2013/842* (2013.01); *A61F 2013/8408* (2013.01); *A61F 2013/8411* (2013.01); *A61F 2013/8414* (2013.01)

(58) Field of Classification Search
CPC ...... A61F 2013/8408; A61F 2013/8411; A61F 2013/8414; A61F 2013/842; A61F 2013/8423; A61F 2013/8426; A61F 2013/8429; A61F 2013/8432; A61F 2013/8435; A61L 15/46
See application file for complete search history.

(56) References Cited

U.S. PATENT DOCUMENTS

| | | | |
|---|---|---|---|
| 5,019,062 A * | 5/1991 | Ryan ................... | A61F 13/8405 428/137 |
| 5,161,686 A | 11/1992 | Weber et al. | |
| 5,407,442 A | 4/1995 | Karapasha | |
| 6,025,319 A | 2/2000 | Surutzidis et al. | |
| 6,313,371 B1 | 11/2001 | Conant et al. | |
| 6,344,036 B1 | 2/2002 | Ivansson | |
| 6,479,150 B1 | 11/2002 | Liu et al. | |
| 8,168,852 B2 | 5/2012 | Quincy, III | |
| 2004/0018359 A1 | 1/2004 | Haggquist | |
| 2004/0121681 A1* | 6/2004 | Lindsay .............. | A61F 13/8405 442/121 |
| 2004/0122388 A1 | 6/2004 | McCormack et al. | |
| 2004/0266302 A1 | 12/2004 | DiSalvo et al. | |
| 2006/0142709 A1 | 6/2006 | Quincy, III | |
| 2007/0073255 A1 | 3/2007 | Thomas et al. | |
| 2008/0200890 A1 | 8/2008 | Wood et al. | |
| 2008/0251081 A1 | 10/2008 | Claussen et al. | |
| 2009/0155508 A1 | 6/2009 | Chau et al. | |
| 2012/0145008 A1 | 6/2012 | Chau et al. | |
| 2015/0290052 A1 | 10/2015 | Forsgren Brusk et al. | |
| 2017/0027778 A1 | 2/2017 | Stridfeldt et al. | |

FOREIGN PATENT DOCUMENTS

| | | |
|---|---|---|
| CN | 102046213 A | 5/2011 |
| EP | 0 304 952 A2 | 3/1989 |
| EP | 0 389 023 A2 | 9/1990 |
| EP | 0 392 528 A2 | 10/1990 |
| EP | 2 110 018 A1 | 10/2009 |
| FR | 2 462 902 A1 | 2/1981 |
| GB | 2 055 586 A | 3/1981 |
| JP | S49-118299 U | 9/1974 |
| JP | H08-508424 A | 9/1996 |
| JP | 2008-142464 A | 6/2008 |
| JP | 2009-155734 A | 7/2009 |
| JP | 2010-088530 A | 4/2010 |
| RU | 2 360 406 C1 | 7/2009 |
| WO | 91/12029 A1 | 8/1991 |
| WO | 94/22501 A1 | 10/1994 |
| WO | 97/01317 A1 | 1/1997 |
| WO | WO 98/01300 A1 | 1/1998 |
| WO | WO 98/41607 | 9/1998 |
| WO | WO 99/39675 A1 | 8/1999 |
| WO | WO 2004/006967 A1 | 1/2004 |
| WO | WO 2007/06712 A1 | 6/2007 |
| WO | WO 2007/067111 A1 | 6/2007 |
| WO | 2010/119272 A1 | 10/2010 |
| WO | WO 2012/163995 A1 | 12/2012 |

OTHER PUBLICATIONS

International Search Report (PCT/ISA/210) dated Jul. 17, 2013, by the European Patent Office as the International Searching Authority for International Application No. PCT/SE2012/051229.
Written Opinion (PCT/ISA/237) dated Jul. 17, 2013, by the European Patent Office as the International Searching Authority for International Application No. PCT/SE2012/051229.
International Preliminary Report on Patentability (PCT/IPEA/409) dated Dec. 4, 2014 for International Application No. PCT/SE2012/051229.
Chinese Office Action dated Nov. 25, 2015 for Application No. 201280076983.6 with English language translation, pp. 1-2.
International Search Report (PCT/ISA/210) dated Sep. 8, 2014, by the European Patent Office as the International Searching Authority for International Application No. PCT/SE2013/051603.
Written Opinion (PCT/ISA/237) dated Sep. 8, 2014, by the European Patent Office as the International Searching Authority for International Application No. PCT/SE2013/051603.
Written Opinion of the International Preliminary Examining Authority (PCT/IPEA/408) dated Dec. 7, 2015, by the European Patent Office for International Application No. PCT/SE2013/051603.
International Preliminary Report on Patentability (PCT/IPEA/409) dated Mar. 3, 2016, by the European Patent Office for International Application No. PCT/SE2013/051603.
International Search Report (PCT/ISA/210) dated Sep. 5, 2014, by the European Patent Office as the International Searching Authority for International Application No. PCT/SE2013/051602.
Written Opinion (PCT/ISA/237) dated Sep. 5, 2014, by the European Patent Office as the International Searching Authority for International Application No. PCT/SE2013/051602.
Written Opinion of the International Preliminary Examining Authority (PCT/IPEA/408) dated Nov. 25, 2015, by the European Patent Office for International Application No. PCT/SE2013/051602.
International Preliminary Report on Patentability (PCT/IPEA/409) dated Feb. 9, 2016, by the European Patent Office for International Application No. PCT/SE2013/051602.
Office Action dated Feb. 17, 2017, by the Russian Patent Office in corresponding Russian Patent Application No. 2015122649/15(035409) and an English Translation of the Office Action. (10 pages).
Office Action dated Mar. 28, 2017, by the Colombia Patent Office in corresponding Colombian Patent Application No. 15134574. (11 pages).
Office Action (Decision of Rejection) dated Feb. 6, 2017, by the Japanese Patent Office in Japanese Patent Application No. 2015-541740, and an English Translation of the Office Action. (9 pages).
Office Action (Notice of Reasons for Rejection) dated Aug. 21, 2017, by the Japanese Patent Office in corresponding Japanese Patent Application No. 2016-541025, and an English Translation of the Office Action. (13 pages).
Office Action dated Sep. 4, 2017, by the Colombian Patent Office in Colombian Patent Application No. NC2016/0000059, and an English Translation of the Office Action. (19 pages).
Office Action (Notice of Reasons for Rejection) dated Sep. 4, 2017, by the Japanese Patent Office in Japanese Patent Application No. 2016-540966, and an English Translation of the Office Action. (10 pages).
Office Action dated Oct. 6, 2017, by the Russian Patent Office in Russian Patent Application No. 2016129457/12(045773). (3 pages).
Office Action dated Jul. 6, 2017, by the Russian Patent Office in Russian Patent Application No. 2015122649/15 (035409) and an English Translation of the Office Action. (11 pages).
The extended European Search Report dated Jun. 29, 2017, by the European Patent Office in European Patent Application No. 13899538.6-1308. (8 pages).

(56) References Cited

OTHER PUBLICATIONS

The extended European Search Report dated Jul. 20, 2017, by the European Patent Office in corresponding European Patent Application No. 13899550.1-1453. (7 pages).

* cited by examiner

ABSORBENT PRODUCT COMPRISING AN ODOR CONTROL MATERIAL

TECHNICAL FIELD

The present invention relates to an absorbent product having a fluid permeable surface and a liquid impermeable opposite surface, wherein the absorbent product comprising an odor control material comprising a carrier material and a plurality of odor control particles adhered to the carrier material.

BACKGROUND

Odor prevention in connection with the use of absorbent products, such as incontinence products, is an important comfort factor for consumers. Bodily fluid, such as urine, is collected and stored in absorbent products and odors may easily arise. It is important for the wearer that these odors do not spread into the environment. The wearer needs to feel safe when using absorbent products both in respect of leakage and odor prevention or control.

In the field of absorbent products, several different solutions are used to prevent odors. For example, odors can be masked by the use of perfumes or deodorizing compounds. Odors may also be adsorbed or absorbed to particles having a large surface area, such as activated carbon, zeolite and starch-based particulate materials. Acidic and/or alkaline odors may be neutralized by the use of substances like baking soda and/or citric acid. For bacteria inhibition, substances having low pH or metal salts can be used. Accordingly, different odor control agents may be used to prevent odors in different manners.

Odor control agents in particle form, such as activated carbon, zeolite and starch-based materials, have been proved to have excellent odor-adsorbing characteristics due to the large surface area of the particles. However, there are some drawbacks related to the use of such odor control agents which may be in a powder form, for example, such powders are very difficult to handle in dry processes due to dusting problems. Powders may contaminate both process equipment and products.

In the prior art, there have been attempts to decrease dusting problems of powders as for example disclosed by EP0392528, in which particles of odor control agent is bond to a fibrous base web, such as non-woven or paper web. The porous base web is dipped in a saturated slurry containing the odor-absorbing particles and a binding agent, together with a surfactant. The excess slurry is then squeezed from the web and the web is dried.

Odor control agent in particle form may also be difficult to disperse in an even manner in the absorbent products. For example, humidity of the atmosphere may cause the particles to build lumps, and this may cause an uneven distribution in the production process and consequently in final products.

Since certain odor adsorbing particles such as for example activated carbon particles are hydrophobic it is also important that these particles do not impair the absorption properties in the product.

Thus, there is still a need to improve the handling of odor control agents in particle form during the production of absorbent products and also a need to secure that the odor adsorbing/absorbing properties as well as the liquid absorption properties are maintained or improved.

DESCRIPTION OF INVENTION

It is an object of the present invention to provide an absorbent product having an efficient odor control system. It is a further object of the present invention to improve the distribution of the odor control particles in the final products so that an efficient odor control system can be obtained without impairing the absorption properties in the final product. It is a further object of the present invention to improve the handling of odor control particles in the production process.

The objects are achieved by an absorbent product having a fluid permeable surface and a liquid impermeable opposite surface, wherein the absorbent product comprising an odor control material comprising a carrier material and a plurality of odor control particles adhered to the carrier material. Furthermore, the carrier material has a first surface located towards the fluid permeable surface of the absorbent product and a second opposite surface located towards the liquid impermeable surface of the absorbent product, wherein the plurality of odor control particles are bonded to the second surface of the carrier material with a water soluble binder substance. The water soluble binder substance has the ability to at least partly dissolve when in contact with an aqueous solution. By having the plurality of odor control particles bonded to the surface of the carrier layer which is located towards the liquid impermeable surface of the absorbent product, the aqueous solution from the user enters the binder substance before it enters the odor control particles. The aqueous solution from the user, such as the urine, can in this way dissolve the binder quickly. In this way a large amount of the total surface area on the odor control particles are available for odor adsorbing.

The absorbent product may comprise a fluid permeable topsheet and a liquid impermeable backsheet and an absorbent core enclosed between the topsheet and backsheet wherein the odor control material is located between the topsheet and the absorbent core with the second surface of the carrier material located towards the absorbent core.

The odor control particles may be activated carbon, zeolite or starch based odor control particles or a mixture thereof. So, if for example the odor control particles are activated carbon particles, the aqueous solution from the user, such as urine, enters the carrier material first, thereafter the binder substance, and finally the activated carbon particles. Since it is important for the odor adsorption that the carbon particles have a large surface area, it has turned out to be important that the aqueous solution from the user very quickly enters the binder substance so that the binder substance can dissolve and release the activated carbon particles from the carrier material so that most of the surface area of the activated carbon particles are utilized for odor adsorption.

According to one embodiment has the water-soluble binder substance a molecular weight of 40 kDa or lower.

The water-soluble binder may comprise a hydrophilic polymer such as polyvinylpyrrolidone, polyethyleneoxide polyacrylics, starch or derivatives of starch.

The water-soluble binder may comprise hydrophilic low molecular weight compounds such as monosaccharides such as glucose or similar, di saccharides such as sucrose or similar, sugar alcohols such as xylitol or similar or polyols such as polyethylene glycol or similar.

The water-soluble binder may also comprise a mixture of a hydrophilic polymer such as polyvinylpyrrolidone, polyethyleneoxide polyacrylics, starch or derivatives of starch and low molecular weight compounds such as monosaccharides such as glucose or similar, di saccharides such as sucrose or similar, sugar alcohols such as xylitol or similar or polyols such as polyethylene glycol or similar.

The binder needs to dissolve, at least partly, immediately after the liquid has wetted the odor control material. By immediately is meant within less than 2 seconds after the liquid reaches the binder substance.

According to one embodiment may the water-soluble binder substance also comprise an additive such as plasticizer, stabilizer, agent improving dispersibility, pH regulating agent, antimicrobial substances or surfactants.

An advantage with a water-soluble binder substance comprising a surfactant or a mixture of different surfactants, is that the water-soluble binder substance is more easily dissolved in an aqueous solution than without surfactant.

According to one embodiment is the weight ratio water-soluble binder substance to odor control particles from 1:10 to 10:1.

The carrier material may be a nonwoven material, a tissue material or a foam material. The nonwoven or tissue may have a surface weight between 15 and 40 $g/m^2$, or 18-25 $g/m^2$. The foam material may have a surface weight between 15 and 100 $g/m^2$.

According to one embodiment is at least one of the surfaces of the carrier material treated with a surfactant. The surfactant may also be applied to both surfaces of the carrier material. The surfactant may be applied to the surface(s) of the carrier material in one separate step with the binder substance thereafter applied in a separate step. However, according to another embodiment the surfactant is mixed with the binder and thereafter the mix is applied. It may also be possible to treat the carrier material with a surfactant in a separate step, as well as having surfactant(s) mixed with the binder substance.

According to yet another embodiment is the carrier material perforated or slitted to cause openings. However, it is essential that the liquid comes into contact with the water-soluble binder substances. Otherwise, the water-soluble binder substances will not be able to dissolve. Therefore, it is an advantage with many apertures having a small size compared to few apertures having a larger size.

The odor control material may cover 5-100% of the total surface area in the horizontal plane of the absorbent product. In another embodiment, the odor control material may cover 5-60% of the total surface area in the horizontal plane of the absorbent product.

SHORT DESCRIPTION OF FIGURES

Examples of different embodiments according to the present invention are further illustrated in the accompanying figures.

DETAILED DESCRIPTION OF FIGURES

Figure 1:
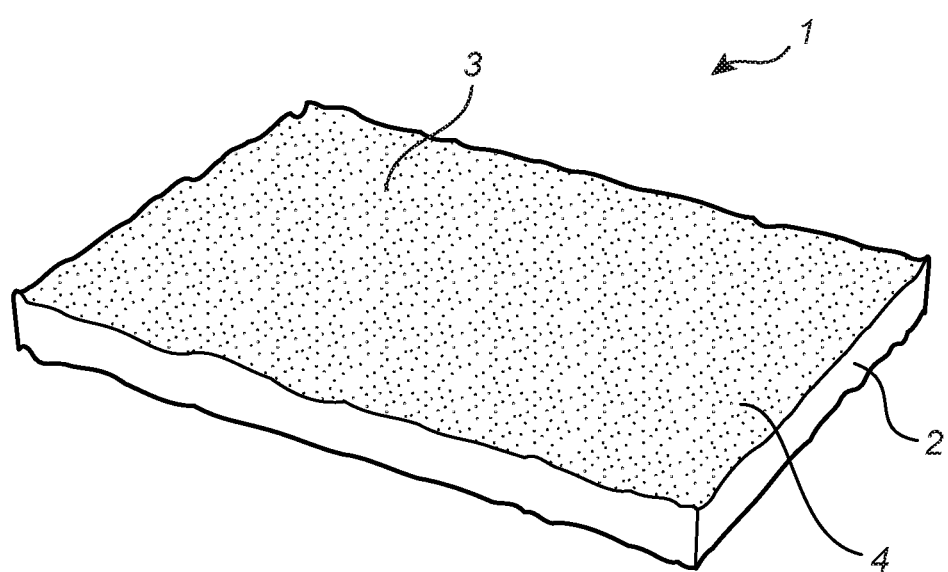
FIG. 1 shows an odor control material according to the invention.

FIG. 1 shows an odor control material 1 according to the invention. The odor control material 1 comprising a carrier material 2 having a first surface 3. A plurality of odor control particles 5 are bonded to the second surface 4 of the carrier material 2 with a water soluble binder substance wherein the binder substance at least partly dissolves when in contact with an aqueous solution.

The particles of the activated carbon 5 may have a particle size of from about 0.1-1000 µm and is preferably from about 1 µm to about 250 µm, measured according to ASTM D5158. Particles having a size smaller than 0.1 µm are often difficult to handle. On the other hand, particles which are larger than 250 µm may feel uncomfortable or uneven in final products where the odor control agent is used, e.g. in absorbent products. Therefore, the particles should be sufficiently fine or small so that they do not cause for example skin irritation.

The specific surface area depends on the physical properties of the product, for example may the BET specific surface area of starch-based particulate agent be from about 5 $m^2/g$-500 $m^2/g$. The larger the specific surface area of the particles is, the better the odor adsorbing property is.

The binder dissolves at least partly thereby parts of the surface of activated carbon particles is free from binder substance which enable the efficiency to adsorb odorous substances to increase. Preferably, the water-soluble material dissolves completely in water or the aqueous solution.

Figure 2A:
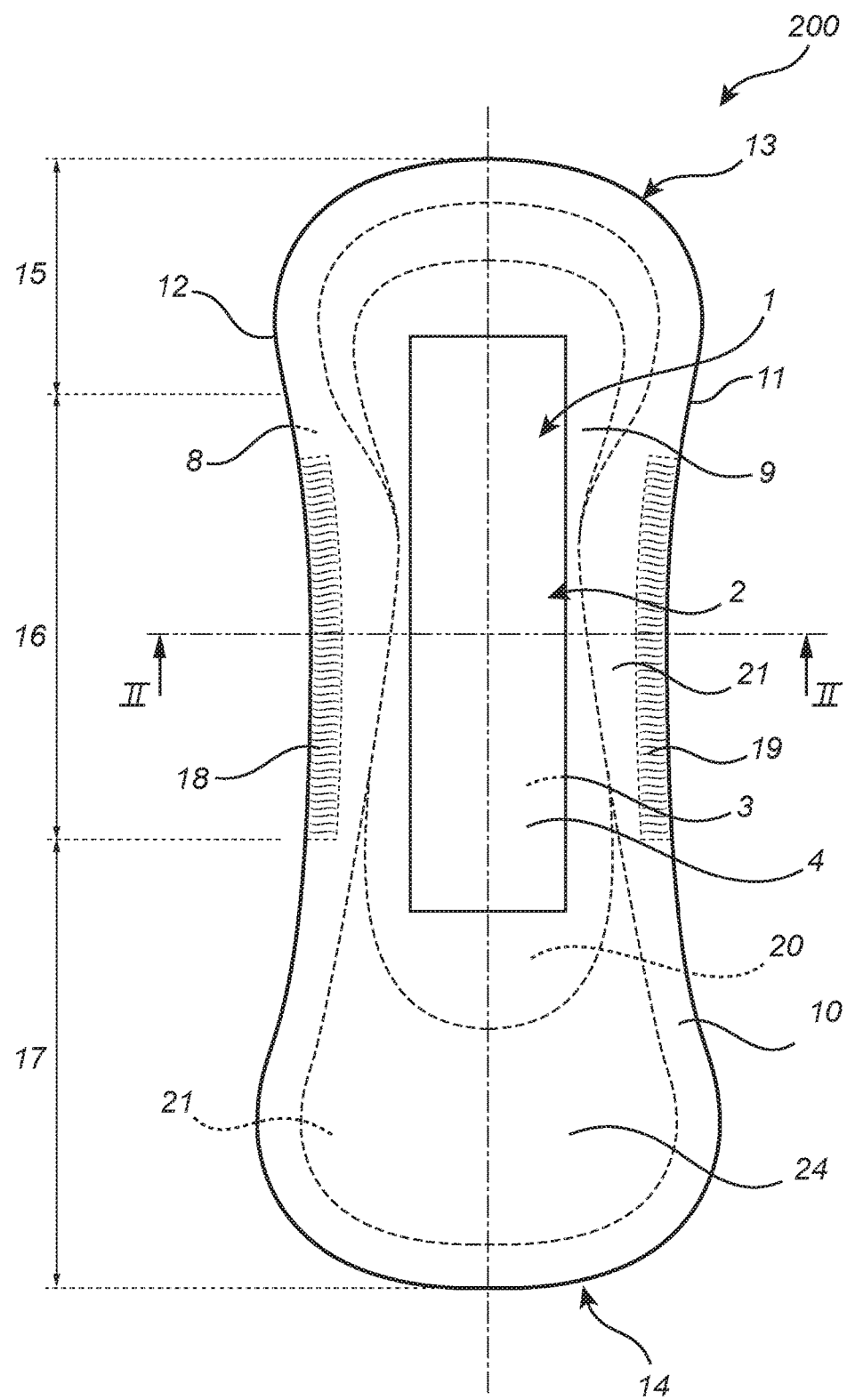
FIG. 2A shows an absorbent product comprising the odor control material seen from the side which will be facing the user when it is being worn.
Figure 2B:
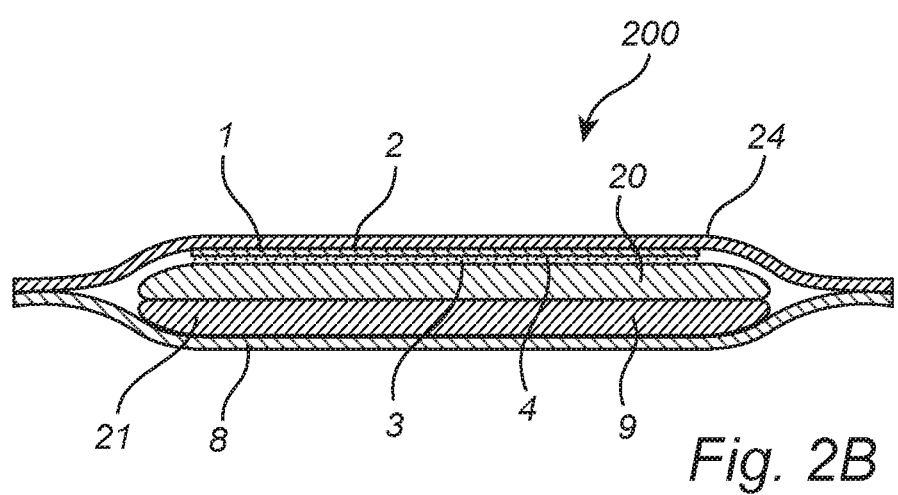
FIG. 2B shows a cross-sectional view of the absorbent product of FIG. 2A, along the line II-II.

The absorbent product shown in FIGS. 2A and 2B is a urine incontinence protector in the form of a pad 200. The pad 200 is seen from the side of the pad that is intended to be facing towards a wearer's body when being worn. The pad 200 comprises a liquid permeable topsheet 24, a liquid impermeable backsheet 8, and an absorbent core 9 enclosed between the topsheet 24 and the backsheet 8, and an odor control material 1 arranged between the topsheet 24 and the absorbent core 9.

The topsheet 24 and the backsheet 8 of the pad 200 extend together laterally outside of the absorbent core 9 along the whole circumference of the absorbent core 9 and is connected to each other in an edge joint 10 around the periphery of the absorbent core 9.

The topsheet 24 consists of any material which is suitable for the purpose, i.e. soft and liquid pervious. Examples of commonly found topsheet 24 materials are nonwoven materials, perforated plastic films, plastic or textile mesh, and fluid permeable foam layers. Laminates consisting of two or more topsheet materials are also commonly employed, as are top sheets consisting of different materials within different parts of the fluid permeable wearer-facing surface.

The backsheet 8 is fluid impermeable. However, backsheet materials that are only fluid repellant may be used particularly in instances where relatively small amounts of urine are expected to be taken up. The backsheet 8 is commonly constituted by a thin, flexible, fluid-impermeable plastic film, but fluid-impermeable nonwoven materials, fluid impermeable foams and fluid impermeable laminates are also contemplated within the scope of the invention. The backsheet 8 may be breathable, implying that air and/or vapor may pass through the backsheet 8. Furthermore, the backsheet 8 may have an outer, garment-facing surface of a textile material such as nonwoven.

The absorbent core 9 may be made up of any suitable absorbent or fluid uptake material as known in the art, such as one or more layers of cellulose fluff pulp, foam, fibre waddings, etc. The absorbent core 9 may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core 9. The fibres may be pulp fibres and the superabsorbent material may be polyacrylate-based particles.

The absorbent core 9 may further incorporate components for improving the properties of the absorbent core 9. Some examples of such components are binder fibers, fluid-dispersing materials, wetness indicators etc., as known in the art.

The pad 200 has an elongate, generally rectangular shape when fully extended in all directions. Any suitable shape may be used for the absorbent product, such as hourglass shape, trapezoidal shape, triangular shape an oval shape, etc. The shape of the product of the invention may be symmetrical about a transverse center line through the product, or may be asymmetrical with end portions having differing shapes and/or differing sizes.

The pad 200 has two longitudinal side edges 11, 12 extending generally in the same direction as a longitudinal center line through the absorbent product. Front and rear end edges 13, 14 typically extend transversely to the longitudinal center line at the ends of the absorbent product. The rear end edge 14 is intended to be orientated rearwards during use of the absorbent article, and the front end edge 13 is intended to be facing forwards towards the abdomen of the wearer. The pad 200 has a front end portion 15, a rear end portion 17 and a crotch portion 16 located intermediate the end portions 15, 17. The crotch portion 16 is a portion which is intended to be placed against the crotch of a wearer during use of the product and to constitute the main acquisition area for body fluid that reaches the pad 200.

The pad 200 may further include fastening means for fastening of the absorbent product inside a supporting pant garment, such as a pair of underpants. The fastening means may be in the form of two longitudinally extending bands of pressure sensitive adhesive arranged on the garment facing surface of the backsheet 8. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

Elastic elements 18, 19 may be arranged along the side edges laterally outside the absorbent core 8. The elastic elements 18, 19 may be bands of elastic material. The elastic elements 18, 19 are optional components of the absorbent product and may be omitted.

The fastening means is optional to the invention and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means may be a mechanical fastener such as hook-type fasteners, clips, press studs, etc. or may be a frictional fastener such as a frictional coating or open-celled foam. Combinations of different types of fasteners are also conceivable.

The odor control material 1 in FIG. 2A is situated above the absorbent core 9 and beneath and in direct contact with the topsheet 24. However, it is also possible that the absorbent product comprises a liquid acquisition and distribution layer and the odor control material may in such a product be situated between the liquid acquisition and distribution layer and the absorbent core, or between other layers in the product. The absorbent core 9 of the pad 200 comprises a first absorbent layer 20 and a second absorbent layer 21. The odor control material 1 may also be arranged in the absorbent product between the first absorbent layer 20 and the second absorbent layer 21.

The absorbent layers 20, 21 may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibers and superabsorbent material, wherein the ratio of superabsorbent material to fibers may vary in the layer.

The first and second absorbent layers 20, 21 may have any suitable shape, such as an hourglass shape with widened end portions and a narrow portion in the crotch portion, or a rectangular shape. The second absorbent layer 21 is placed below the first absorbent layer 20. The first absorbent layer 20 is smaller than the second absorbent layer 21. The second absorbent layer 21 extends further forward and rearward in the absorbent product than the first absorbent layer 20. However, the absorbent core may also comprise only one single layer or may comprise one or more further absorbent layers. The size of the different layers may also vary, and the absorbent core 9 described in FIGS. 2A and 2B is only one illustration of an absorbent core suitable for the present invention.

The odor control material 1 in the absorbent product 20 illustrated in FIGS. 2A and 2B has a rectangular shape and may be surrounded in the longitudinal and lateral directions by portions of the absorbent core. Other shapes and configurations for the odor control material 1 may also be used.

In FIG. 2B a cross-sectional view of the absorbent product of FIG. 2A is shown, along the line II-II. So, the pad 200 has a liquid permeable top sheet 24, a liquid impermeable back sheet 8, and an absorbent core 9 enclosed between the top sheet 24 and the back sheet 8 and the odor control material 1 is located between the topsheet 24 and the absorbent core 9. In FIG. 2B it is also shown that the carrier material 2 has a first surface 22 and a second opposite surface 23 wherein the first surface 22 is facing the liquid permeable topsheet 4 and the second surface 23 is facing the absorbent core 9. Furthermore, the odor control particles 3 are bonded to the second surface 23 of the carrier material 2 so that the surface bonded with odor control particles 3 is facing the absorbent core 9.

EXAMPLES

Example 1—Specific Surface of Activated Carbon Particles

This test was performed to compare the specific surface for activated carbon particles covered with water-soluble binder substance before the sample has been wetted and after the sample has been wetted. Also a sample having no water-soluble binder substance has been measured. The specific surface area of the particles determines the area of the substance that is available for adsorption and/or interaction with other substances. The specific surface area in this context is defined as BET-surface area. The BET-theory describes the adsorption of gas molecules to a solid surface and is based upon an assumption for the energy for the adsorption of the first layer. By measuring the volume of the gas after desorption the specific surface area is calculated. The method has been developed by Brunauer, Emmett and Teller (BET). The skilled person would know conventional instruments for performing the measurement.

Tested Samples
1. Activated carbon particles without binder substance
2. Activated carbon particles covered with water-soluble binder substance. The water-soluble substance is polyvinylpyrrolidone with a molecule weight 40 kDa.
3. Activated carbon particles covered with water-soluble binder substance. The water-soluble substance is polyvinylpyrrolidone with a molecule weight 40 kDa. After the sample has been covered with the water-soluble binder substance, the sample has been wetted. The wetting procedure is as follows: 50 ml 0.9% saline solution having a temperature of 35 degree Celsius is poured carefully over the sample and filtered by water suction. A Buchner funnel with a wet filter is used. Then the filter with the sample is dried in an oven having a temperature of 80 degree Celsius during 24 hours. Thereafter the sample has been grinded.

BET-measurements have been made on these three samples with the following result:

| Sample | Specific surface ($m^2/g$) |
| --- | --- |
| Activated carbon particles without binder substance | 591 |
| Activated carbon particles with water-soluble binder substance (not wetted) | 131 |
| Activated carbon particles with water-soluble binder substance (wetted) | 238 |

The result shows that the sample with activated carbon particles covered with water-soluble binder substance, but not wetted, has less specific surface then the sample after wetting. So, by wetting the sample, the available specific surface is strongly increased, from 131 $m^2/g$ to 238 $m^2/g$.

The specific surface for the sample with no binder substance, the untreated active carbon particles, has a higher specific surface. However, as previously described, such powders are very difficult to handle in dry processes due to dusting problems. Powders may contaminate both process equipment and products.

Example 2—Dissolution of Binder Substance

This test was performed to investigate how much of the binder substance that was dissolved in one minute in a tempered saline solution.

Materials:
Saline solution, temperature 35-37° C.
Vortex apparatus IK MS2, speed 1500 rpm
Test tube 15 ml
Filter paper, 2 layers, Tork 23 g/m2
Funnel
Binder substance, thickness 300-2000 μm, with 50 weight-% of activated carbon

| Sample | Molecule weight | Water-solubility |
| --- | --- | --- |
| A (Polyethylene oxide polymer) | 100 kDa | water-soluble |
| B (Polyethylene oxide polymer) | 600 kDa | water-soluble |
| C (Mixture of saccharose and glucose) less than | 40 kDa | water-soluble |
| D (Styrene-acrylate copolymer) | | not water-soluble |

0.02 g of the binder substance with activated carbon was added to the test tube. Each material was in 1 to 3 pieces. Three ml of the tempered saline solution was poured into the test tube which was instantly placed on the Vortex. After 1 minute the content of the test tube was filtered. After filtration the filter paper was folded up and a visual assessment was made with respect to the proportion of the material which had been dissolved and/or softened and distributed on the filter paper.

| Polymer carrier matrix | Dissolution % |
| --- | --- |
| Sample A | >90 |
| Sample B | >90 |
| Sample C | 100 |
| Sample D | 0 |

The dissolution for sample C, the water-soluble binder substance of a mixture of saccharose and glucose having a molecule weight less than 40 kDa was 100%, wherein the reference sample D of a water-insoluble binder substance was 0%. Sample A and B of water-soluble binder substance having a molecule weight more than 40 kDa, have a dissolution that is less than 100%. So, sample C, which is within the scope of the present invention, is the only sample having a dissolution of 100%.

Example 3—Measurement of Specific Surface Area in an Absorbent Structure

The odor control particles in example 3 have been activated carbon particles. The odor control material has been placed on top of an absorbent core with the second surface of the carrier material having the activated carbon particles bonded to it, facing the absorbent core. Therefore, the specific surface area ($m^2/g$) in example 3, is the surface area ($m^2$) of the carbon particles, per gram (g) of the total weight of the material. The total weight of the material in example 3 is the sum of the weight of the odor control material and the weight of the absorbent core. The absorbent core was composed of cellulose fibers and superabsorbent particles and the weight of the absorbent core was about 990 $g/m^2$.

The specific surface area in this context is defined as BET-surface area. The skilled person would know conventional instruments for performing the measurement. The larger the specific surface area of the particles is, the better the odor adsorbing property is.

Tested Samples
Sample 1
Absorbent core and odor control material, wherein particles of activated carbon are bonded to the second surface of the carrier material with a water insoluble binder substance.
Sample 2
Absorbent core and odor control material, wherein particles of activated carbon are bonded to the second surface of the carrier material with a water soluble binder substance. The water-soluble binder substance is polyvinylpyrrolidone with a molecular weight 40 kDa.

The only difference between sample 1 and sample 2 is that in sample 1 the binder substance is water-insoluble and in sample 2 the binder substance is water-soluble.

Results

| | Before wetting ($m^2/g$) | After wetting and drying ($m^2/g$) |
| --- | --- | --- |
| Sample 1 | 13 | 11 |
| Sample 2 | 12 | 25 |

The result shows that when the plurality of odor control particles are bonded to the second surface of the carrier material by a water-soluble binder, as in sample 2, compared to when the plurality of odor control particles are bonded to the second surface of the carrier material by a water-insoluble binder, as in sample 1, the available specific surface area is increased by more than 100%.

Example 4—Positioning of Odor Control Material in Absorbent Product

A sensory evaluation was performed to investigate how the position of the odor control material in the thickness direction of the product influenced the odor inhibition; close to the backsheet, in the middle of the product between two layers in the absorbent core, or just below the topsheet.

Tested Absorbent Products:
1. Incontinence pad without odor control material (reference)
2. Incontinence pad with odor control material directly above the backsheet
3. Incontinence pad with odor control material between layers in the absorbent core
4. Incontinence pad with odor control material directly below the topsheet The incontinence pad had a topsheet, a backsheet and an absorbent core there between. The absorbent core comprised two layers, wherein the first layer was facing the topsheet and the second layer was facing the backsheet. The first layer facing the topsheet had a smaller total surface area in the plane of the pad than the second layer. The odor control material had the same size (surface area) as the first absorbent layer. The first absorbent layer covered about 50% of the total surface of the incontinence pad so therefore also the odor control material covered about 50% of the total surface of the incontinence pad. The odor control material was placed at three different positions in the products; on top of the product, between the absorbent cores and in the bottom of the product. An odor solution containing Diacetyl (250 ng/ml), Dimethyl trisulfide (14 ng/ml) and 3-methyl butanal (40 ng/ml), was added to each product before the odor evaluation took place.

The odor control particles were activated carbon particles and the carrier material was a foam material.

There were 11 panelists. The panelists were asked to judge the odor intensity of the test products and to put a mark on a line scale, labeled from very weak (0) to very strong (1). The relatively odor intensity for the reference product without an odor control material was set to 1 on the line scale.

The mean values calculated from the panelists' judgments gave the following results:

| Product | Rel. odor intensity |
| --- | --- |
| 1. Incontinence pad without odor control material (reference) | 1 |
| 2. Incontinence pad with odor control material directly above the backsheet | 0.9 |
| 3. Incontinence pad with odor control material between layers in the absorbent core | 0.6 |
| 4. Incontinence pad with odor control material directly below the topsheet | 0.5 |

The outcome of this sensory evaluation indicates that the placement of the activated carbon matters, less smell when it was placed directly below the topsheet, more when it was placed between the two absorbent cores and most when it was placed in the bottom of the product.

Example 5—Activated Carbon Particles on One Surface of a Carrier Material Compared to Activated Carbon Particles on Both Surfaces of a Carrier Material A carrier material has a first surface and an opposite second surface. The odor inhibition has been measured for a carrier material having activated carbon bonded to the first surface as well as to the second surface. The odor inhibition has also been measured for a carrier material with activated carbon on only the second surface of the carrier material. The odor inhibition has also been measured for an incontinence pad without odor control material.

Tested Absorbent Products:
1. Incontinence pad without odor control material (reference)
2. Incontinence pad with a foam coated with activated carbon on both surfaces
3. Incontinence pad with a foam coated with activated carbon on only one surface For the incontinence pad 2, each surface of the foam was coated with 25 gsm of activated carbon so the total amount of carbon was 50 gsm. For the incontinence pad 3 where the foam in the absorbent product was coated with activated carbon on only one surface, this surface was coated with 50 gsm carbon. Hence, the total amount of carbon was the same for absorbent product 2 and absorbent product 3.

Odor reduction was evaluated in the following way: A cocktail with diacetyl, 3-methylbutanal, DMTS and p-cresol was added to the incontinence pad. The incontinence pad was placed in air-tight glass-chambers, and left for incubation at 35° C. so equilibrium could be reached between the solution and the head space. The head space was sampled by a SPME-fiber (solid phase micro extraction-fiber) followed by analysis with a GC-MS (gas-chromatography-mass spectrometry) system. The individual odor substances were detected and odor reduction was calculated by dividing the peak area for the sample with activated carbon particles by the peak area for the sample without activated carbon particles. Sample with activated carbon particles were only compared to samples without activated carbon particles (reference) where the same batch of odor cocktail has been used, and samples with activated carbon particles and samples without activated carbon particles (reference) was always analysed on the same day.

Result:

| Product | Diacetyl | 3-Metylbutanal | DMTS | p-Cresol |
| --- | --- | --- | --- | --- |
| 1. | 1 | 1 | 1 | 1 |
| 2. | 0.03 | 0.12 | 0.03 | 0.15 |
| 3. | 0.03 | 0.15 | 0.04 | 0.18 |

No difference in odor reduction could be seen between the incontinence pad 2 having carbon particles coated on both surfaces compared to the incontinence pad 3 having carbon particles coated only on one surface, so the odor reduction is not reduced when having the carbon particles only on one side.

The invention claimed is:
1. Absorbent product having a liquid permeable surface and a liquid impermeable opposite surface, wherein the absorbent product comprises an odor control material com- prising a carrier material and a plurality of odor control particles adhered to the carrier material, the absorbent product comprising a liquid permeable topsheet, a liquid impermeable backsheet and an absorbent core enclosed between the topsheet and backsheet, wherein:

the odor control material is located between the topsheet and the absorbent core;

the carrier material has a first surface located towards the liquid permeable surface of the absorbent product and a second opposite surface located towards the absorbent core, the plurality of odor control particles consists of activated carbon and is bonded to the second opposite surface of the carrier material with a water soluble binder substance wherein the binder substance at least partly dissolves when in contact with an aqueous solution, and the plurality of odor control particles is only on the second opposite surface of the carrier material.

2. Absorbent product according to claim 1, wherein the water-soluble binder substance has a molecular weight of 40 kDa or lower.

3. Absorbent product according to claim 2, wherein the water-soluble binder substance comprises a hydrophilic polymer.

4. Absorbent product according to claim 2, wherein the water-soluble binder substance comprises a hydrophilic low molecular weight compound.

5. Absorbent product according to claim 1, wherein the first surface of the carrier material is treated with surfactant(s).

6. Absorbent product according to claim 1, wherein the water-soluble binder substance comprises an additive selected from the group of plasticizer, stabilizer, agent improving dispersibility, pH regulating agent, antimicrobial substance, surfactant(s), and a mixture thereof.

7. Absorbent product according to claim 1, wherein the weight ratio binder substance to odor control particles is from 1:10 to 10:1.

8. Absorbent product according to claim 1, wherein the carrier material is a nonwoven material.

9. Absorbent product according to claim 1, wherein the carrier material is a foam material.

10. Absorbent product according to claim 1, wherein the odor control material covers 5-100% of the total surface area in a horizontal plane of the absorbent product.

11. Absorbent product according to claim 1, wherein the odor control material covers 5-60% of the total surface area in a horizontal plane of the absorbent product.

12. Absorbent product according to claim 1, wherein the carrier material is perforated or slitted for providing openings.

13. Absorbent product according to claim 3, wherein the hydrophilic polymer is a polyvinylpyrrolidone, polyethyleneoxide polyacrylic, starch or derivative of starch.

14. Absorbent product according to claim 4, wherein the hydrophilic low molecular weight compound is a monosaccharide, disaccharide, sugar alcohol, or polyol.

* * * * *